(12) United States Patent
Huang et al.

(10) Patent No.: US 8,409,835 B2
(45) Date of Patent: Apr. 2, 2013

(54) METHOD FOR PRODUCING XYLITOL FROM LIGNOCELLULOSIC HYDROLYSATES WITHOUT DETOXIFICATION

(75) Inventors: Chiung-Fang Huang, Taipei (TW); Yi-Feng Jiang, Taoyuan County (TW); Ting-Hsiang Lin, Taoyuan County (TW); Gia-Luen Guo, Taipei County (TW); Wen-Song Hwang, Taoyuan County (TW); Jia-Baau Wang, Taipei (TW)

(73) Assignee: Institute of Nuclear Energy Research Atomic Energy Council, Executive Yuan, Taoyuan County (TW)

( * ) Notice: Subject to any disclaimer, the term of this patent is extended or adjusted under 35 U.S.C. 154(b) by 322 days.

(21) Appl. No.: 12/775,655

(22) Filed: May 7, 2010

(65) Prior Publication Data
US 2011/0097772 A1 Apr. 28, 2011

(30) Foreign Application Priority Data
Oct. 23, 2009 (TW) .............................. 98135912 A

(51) Int. Cl.
*C12P 7/18* (2006.01)
*C12N 9/00* (2006.01)
*C12N 1/00* (2006.01)
*C12N 15/00* (2006.01)
*C07H 21/04* (2006.01)

(52) U.S. Cl. ..................... 435/158; 435/183; 435/255.1; 435/255.4; 435/320.1; 536/23.2

(58) Field of Classification Search ....................... None
See application file for complete search history.

(56) References Cited

U.S. PATENT DOCUMENTS

2006/0201641 A1* 9/2006 Harris et al. .................... 162/37
2006/0246563 A1* 11/2006 Eroma et al. .................. 435/158

OTHER PUBLICATIONS

Mohagheghi et al. Process Biochemistry 41(2006) 1806-1811.*

* cited by examiner

*Primary Examiner* — Christian Fronda
(74) *Attorney, Agent, or Firm* — WPAT PC; Justin King

(57) ABSTRACT

A method for producing xylitol by fermentation of lignocellulosic hydrolysates without detoxification is provided. By using the originally isolated yeast *Candida* sp., xylose can be effectively converted into xylitol. The invention also provides the *Candida* strain having high furfural tolerance, and is capable to produce xylitol from various types of non-detoxified lignocellulosic hydrolysates, in which the overall utilization of xylose in hydrolysate can reach over 95%.

3 Claims, 3 Drawing Sheets

• Operation steps of overliming conditioning

• Operation steps of conditioning without detoxification

METHOD FOR PRODUCING XYLITOL FROM LIGNOCELLULOSIC HYDROLYSATES WITHOUT DETOXIFICATION

BACKGROUND OF THE INVENTION

1. Field of the Invention

The present invention relates to a method for producing xylitol from lignocellulosic hydrolysates without detoxification, in which the xylose fermentation strain *Candida* sp. shows high furfural tolerance and is used to convert xylose into xylitol from various source of non-detoxified lignocellulosic hydrolysates. The overall utilization of xylose in hydrolysate reach over 95%.

2. Related Art

Xylitol is a rare sugar that exists in low amount and is the constituent of many vegetables and fruits. Xylitol is also one of the intermediate metabolites in the sugars metabolism of mammalian, and its chemical property belongs to the pentitols. The reason why xylitol attracts global attention is that it is a natural sweetener having equivalent sweetness to sucrose with the calorie of merely 60% of sucrose. Medical studies have shown that, xylitol is helpful for the prevention of dental caries, because it is not easily utilized by *Streptococcus mutans* and other microorganisms that may cause tooth decay, and also has the function of maintaining acid-base balance in the mouth. Furthermore, studies also point out that xylitol is rapidly metabolized to generate energy, but the metabolism in human body dose not need insulin participation, so it is widely used as substitute of sucrose in the nutrition for diabetics in clinic presently. Generally, the development of industrial production of xylitol has applications for at least three major industries, that is, food processing industry (for example, baking industry, emulsifiers, stabilizing agents, and chewing gum), odontological prevention and control (dental caries prevention, promotion of tooth re-mineralization and rehardening), and pharmaceutical industry (prevention of upper respiratory tract infection, as sweetener for its high-sweetness and low-calorie properties, nutraceuticals, and vitamin formulations).

Presently, the method of industrial mass production of xylitol includes the following steps. The lignocellulosic biomass material enriched with hemicellulose is pretreated by acid hydrolysis and converted into a hydrolysate with xylose as the main component. Next, the xylose-rich hydrolysate is hydrogenated at high temperature and high pressure with the catalysis of nickel metal and then to produce xylitol from the conversion of xylose. The yield of xylitol produced by this chemical synthesis is about 40-50%, and at the same time, all the sugars present in the hydrolysate are also reduced to their corresponding sugar alcohols. Therefore, in addition to xylitol, other sugar alcohols, such as arabitol and sorbitol, may also exist in the product. These sugar alcohols have similar chemical properties and are relatively difficult to be separated. Furthermore, the production process of chemical synthesis is complex and consumes a great amount of energy, and the equipment cost is high, so the price of xylitol cannot be decreased. In order to decrease the production cost and meet the increasing market demand for xylitol, the industry is actively developing a high yield but low energy-consumption alternative for xylitol production.

The bioconversion method for xylitol production by fermentation of lignocellulosic hydrolysate using microorganisms is the most advantageous and competitive alternative presently, in which by using the naturally occurring xylose-fermenting microorganisms, the xylose is directly converted into xylitol through the physiological metabolism of the microorganisms, and then the xylitol product is then recovered by purification and crystallization. In addition to high production yield, bioconversion method also has the advantage in the elimination of the risk that the xylitol product may be contaminated by heavy metal by the chemical synthesis method. As for the regulation standard for food additives, the xylitol product produced by bioconversion method is relatively safe.

In the relevant literatures currently collected, the type of the hydrolysates discussed in the studies of converting xylose into xylitol by microorganisms include corncob, corn fiber, sugarcane bagasse, hardwood, eucalyptus, walnut shell, brewer's spent grain, prairie grass, wheat straw, and rice straw, etc., among which, there is a large difference in relevant xylitol yield (0.2-0.8 g/g).

Generally, the lignocellulosic biomass material mainly contains 60-80% of cellulose, hemicellulose, and 15-25% of lignin, in which hemicellulose is required to be converted into pentoses (mainly xylose) through a pretreatment process, and then further converted into xylitol by microorganism fermentation. Presently, the pretreatment technology for converting hemicellulose into saccharides mostly adopts high-temperature and high-pressure thermal chemical pretreatment technologies, such as, dilute acid hydrolysis, dilute acid-catalyzed steam explosion to decompose hemicellulose into xylose. During the reaction of such pretreatment technology, generally, a certain proportion of raw material and an aqueous solution are firstly filled into a reactor, and then 1-3% (w/w) of dilute sulfuric acid is added under high-temperature and high-pressure reaction conditions, and the liquid obtained after the reaction is so-called as hydrolysate. In addition to the release of sugars, the pretreatment also generates certain amounts of fermentation inhibitors, such as, acetic acid, furfural, and hydroxymethyl furfural, accompanied with different reaction conditions. Therefore, presently, the xylose-rich hydrolysate obtained by pretreatment is usually treated with detoxification technology, such as, overliming, active carbon adsorption, and ion exchange resin, alone or in combination, such that hydrolysate is subjected to fermentation with microorganisms successfully and converted xylose into the xylitol. For example, for the mostly used overliming method (as shown in FIGS. 1A and 1B), the conditioning of the xylose-rich hydrolysate includes heating, adding excessive lime, solid-liquid separation, and adding an acid agent to adjust the pH value to be weakly acidic, etc. The generated gypsum sludge is required to be further treated and disposed. Because during the conditioning of the overliming method, xylose loss is generally caused, and calcium sulfate sludge is generated, additional cost and equipments for treatment and disposal are required, thus increasing the production cost of xylitol. By comparison, the process without detoxification is simple, and it is only required to add an alkali agent to adjust the pH value of the xylose hydrolysate to be weakly acidic. However, the non-detoxified hydrolysate may contain high concentration of fermentation inhibitors, such as furfural and sulfate ion, so that the difficulty of converting xylose into xylitol by fermentation is increased relatively. Therefore, it is an important issue for reduce the xylose loss as well as the production cost for xylitol to improve the competitiveness of bioconversion-based xylitol production.

SUMMARY OF THE INVENTION

Accordingly, in order to solve the problems as described above, the present invention provides a method for producing xylitol by fermentation of lignocellulosic hydrolysates without detoxification. A xylitol fermentation yeast strain is isolated and screened from the fermentation broth of a 100 liter pentose fermenter in the mini-pilot plant of the Institute of Nuclear Energy Research for cellulosic ethanol research and development, and then molecular analysis of the 18S rDNA sequence has identified the strain as a yeast strain of *Candida* sp. belonging to *Candida* genus. The strain is used to ferment the synthetic xylose solution to produce xylitol, and the maximum yield can be approximately to 0.8 g/g, which is higher than those of xylitol production strains also belonging to *Candida* genus, such as *Candida boidinii*, *Candida guilliermondii*, *Candida utilis*, and *Candida maltosa* (mostly with a xylitol yield of below 0.7 g/g). Meanwhile, the xylitol yield of this newly isolated strain also reaches a leading level, compared with other xylitol-producing stains belonging to different yeast genus.

In addition, the strain of the present invention has high tolerance to the toxic inhibitor furfural, which is often existed in the pretreated lignocellulosic hydrolysate. The fermentation experiments with a synthetic xylose solution supplemented with furfural show that the strain can grow in the xylose solution containing 3 g/L of furfural and produce xylitol, and the yield is very similar to that of the xylose fermentation without furfural.

On the other hand, by using various types of pretreated lignocellulosic hydrolysates, such as, rice straw, silvergrass, sugarcane bagasse, napiergrass, pineapple peel, it is confirmed in the present invention that the strain can indeed directly grow in these lignocellulosic hydrolysates without detoxification, and can effectively convert xylose in the lignocellulosic hydrolysates into xylitol.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

The features and implementation of the present invention are described in detail with preferred embodiments below.

I Results of Xylitol Production by Fermentation of Xylose Solution with *Candida* sp.

Figure 1A:
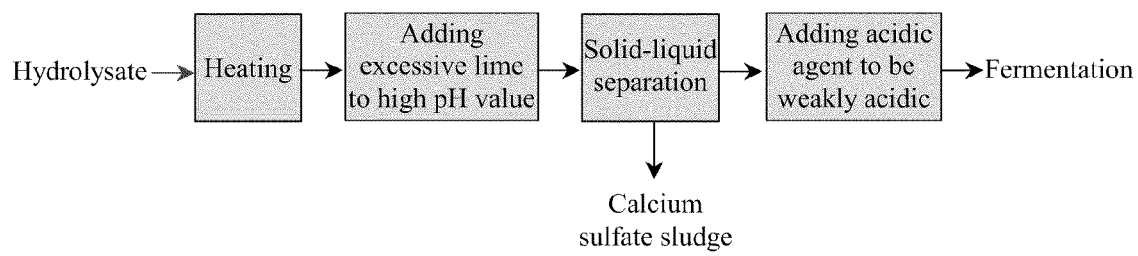
FIGS. 1A and 1B show steps of overliming conditioning and conditioning without detoxification for xylose-rich lignocellulosic hydrolysate.
Figure 1B:
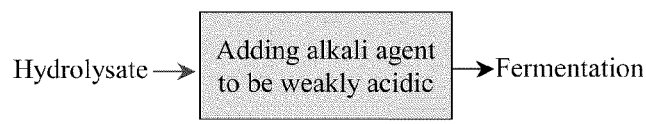
Figure 2:
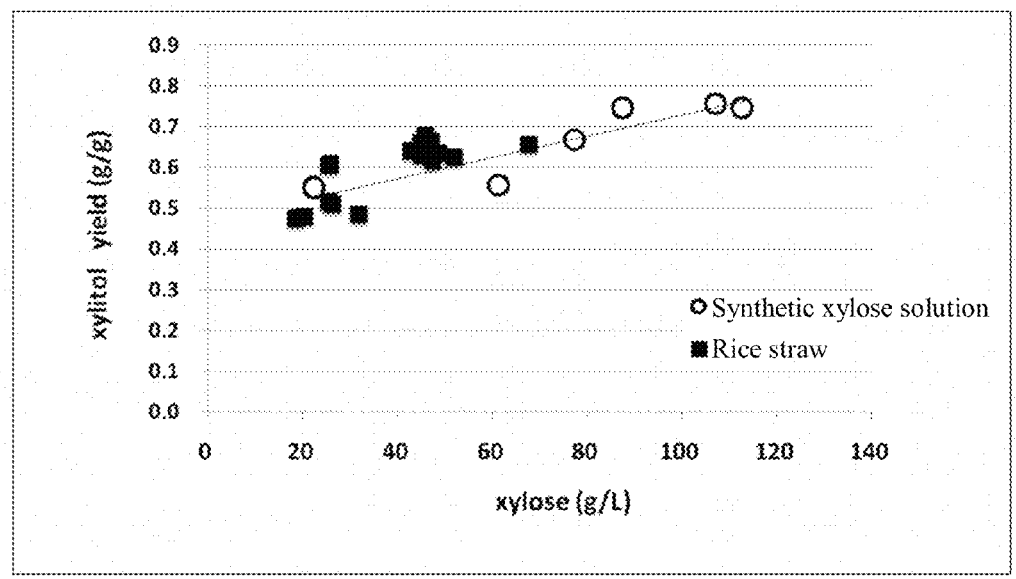
FIG. 2 shows the xylitol yield from the fermentation of synthetic xylose solution and rice straw hydrolysate without detoxification.

The xylitol production from xylose fermentation by *Candida* sp. strain is investigated by a synthetic xylose solution (YPX, medium of yeast extract, peptone and xylose), and the production of xylitol by the yeast strain under different initial xylose concentrations is performed in a 250 mL flask containing 50 mL of fermentation medium. The fermentation parameters are controlled, such that the temperature is 30° C., the agitation of the fermentation is 100 rpm, and the ratio of the inocula size of the culture and the volume of the fermentation medium is 1:6 (v/v). The results are shown in FIG. 2. The initial xylose concentration in the fermentation medium will determine the final yield for xylitol production. As the initial xylose concentration is increased, the xylitol yield of the strain obtained by the fermentation is increased correspondingly in a linear trend. When the xylose concentration is in a range of 20-80 g/L, the yield of xylitol produced by the strain is about 0.55-0.70 g/g; when the xylose concentration is higher than 80 g/L, the yield of xylitol produced by the strain is up to 0.75 g/g. Therefore, the initial xylose concentration surely has influence on the xylitol yield.

II The Tolerance of the Strain *Candida* sp. to Furfural

Figure 3:
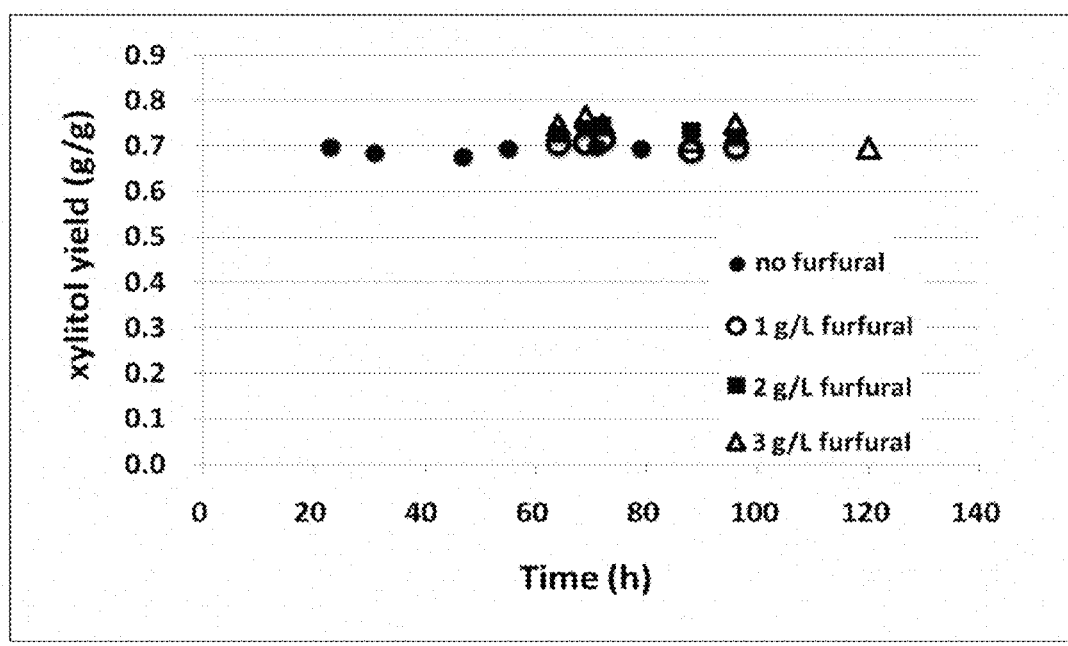
FIG. 3 shows the influence of furfural on the xylitol yield.

The fermentation medium contained 97 g/L sterilized synthetic xylose solution with furfural in a concentration range of 1-3 g/L added. The fermentation temperature is controlled at 30° C., the agitation of the incubator is maintained at 150 rpm, and the ratio of the inocula size of the culture and the volume of the fermentation medium is 1:6 (v/v). The results are shown in FIG. 3. Even at a high concentration of furfural of 3 g/L, the xylose fermentation capacity of the strain is the same as that without furfural, and the xylitol yield for all could be higher than 0.7 g/g, thereby, it is obvious that the tolerance of the strain to furfural is higher than 3 g/L.

Figure 4:
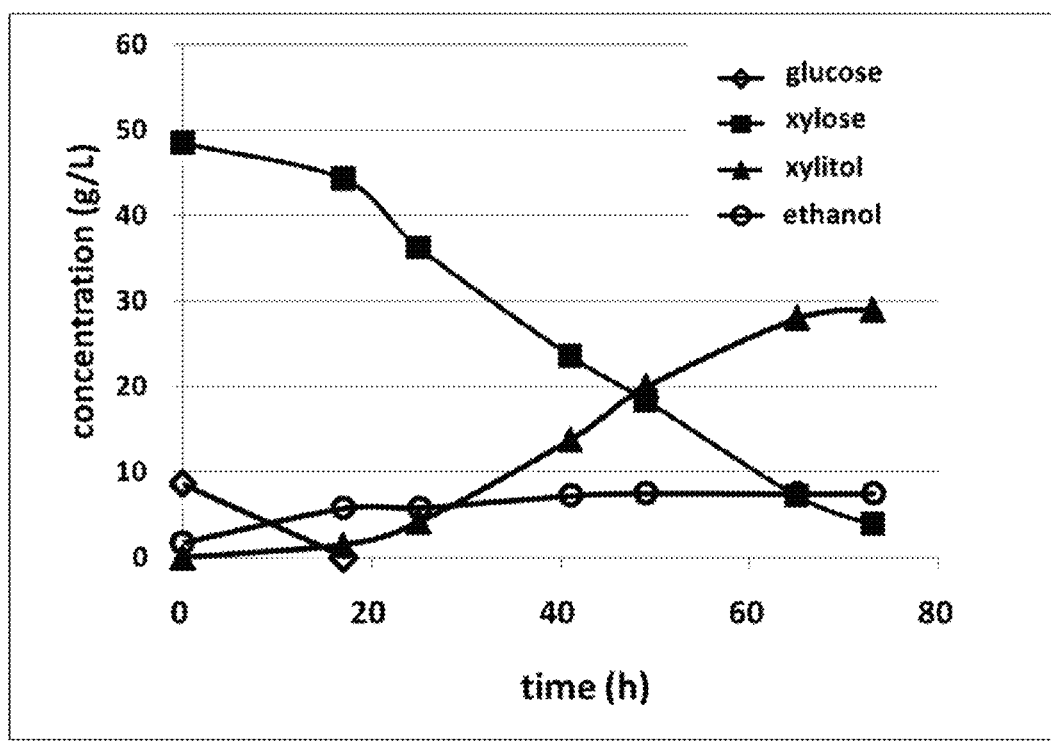
FIG. 4 shows the generation of xylitol by fermentation of rice straw hydrolysate without detoxification.

III Xylitol Production by Fermentation of Rice Straw Hydrolysate without Detoxification Using the *Candida* sp. Strain The rice straw xylose hydrolysate is obtained by a pretreatment facility equipped with a twin-screw extruder and a washing reactor. In the reaction, the suitably sized rice straw is firstly structurally decomposed by the twin-screw extruder, in which the dilute acid concentration is 1-3% (w/w), the screw speed is 40 rpm, the reaction temperature is 120-130° C., the reaction time is 10-20 min, and the ratio of the dry weight of the feeding rice straw and the aqueous solution is about 50:100. After being treated with the extruder, the rice straw is introduced to the washing reactor, into which an appropriate amount of steam is applied, such that the ratio of the dry weight of the rice straw and the aqueous solution is decreased to about 30:100, and at the same time, the reaction temperature is raised to 160° C., and at this temperature, the reactant is boiled for 20 min. Then, the rice straw and the aqueous solution after reaction are discharged, and separated in a solid-liquid separation equipment. The obtained aqueous solution is the xylose-rich hydrolysate, and the main composition is as shown in Table 1. The xylose concentration in the hydrolysate is about 30-35 g/L, NaOH is added into the rice straw hydrolysate to adjust to pH 6.0, the fermentation temperature is controlled at 30° C., the agitation of the incubator is maintained at 100-150 rpm, the ratio of the inocula size of the culture and the volume of the fermentation medium is 1:6 (v/v). The results are shown in FIG. 4. The strain can completely consume xylose in the hydrolysate without detoxification to produce xylitol in a reasonable time. Further compared to the synthetic xylose solution, at the same xylose content, the xylitol production yield of the strain by fermentation of non-detoxified rice straw hydrolysate is even higher compared to fermentation of the synthetic xylose solution (compared with FIG. 2).

TABLE 1

Composition of rice straw xylose hydrolysate

| Composition of hydrolysate | Concentration (g/L) |
| --- | --- |
| Glucose | 6.0~6.5 |
| Xylose | 32.3~35.2 |
| Arabinose | 5.4~5.8 |
| Acetic acid | 1.7~2.2 |
| Furfural | 0.9~1.1 |
| HMF | 0.1~0.3 |

IV Xylitol Production by Fermentation of Sugarcane Bagasse Xylose Hydrolysate without Detoxification Using *Candida* sp. Strain The fermentation medium is a sugarcane bagasse hydrolysate pretreated by dilute acid. For pretreatment, the concentration of the dilute acid is 1-4%, the operation temperature is 130° C., and the reaction time is 15 min at this temperature. In this case, NaOH is added to adjust the pH value of the hydrolysate to 6.0, the fermentation temperature is controlled at 30° C., the agitation of the incubator is maintained at 100 rpm, and the ratio of the inocula size of the culture and the volume of the fermentation medium is 1:6 (v/v). The content of xylose in the sugarcane bagasse hydrolysate is 19.8-25.8 g/L, the content of the inhibitor furfural is 0.14-0.52 g/L, the amount of xylitol produced is 7.74-12.51 g/L, and the overall utilization of xylose is 97.6-99%, as shown in Table 2.

TABLE 2

Xylitol production by fermentation of sugarcane bagasse hydrolysate without detoxification

| time (h) | glucose (g/L) | xylose (g/L) | xylitol (g/L) | ethanol (g/L) | furfural (g/L) |
| --- | --- | --- | --- | --- | --- |
| 0 | 2.27 | 19.82 | | 1.76 | 0.14 |
| 17 | | 10.84 | 3.79 | 3.70 | |
| 25 | | 5.84 | 6.03 | 3.89 | |
| 41 | | 0.48 | 7.74 | 4.49 | |
| 0 | 3.52 | 25.79 | | 1.76 | 0.52 |
| 17 | | 18.99 | 2.51 | 3.86 | |
| 25 | | 13.79 | 5.17 | 4.08 | |
| 41 | | 3.63 | 9.54 | 4.45 | |
| 49 | | 2.22 | 10.77 | 4.87 | |
| 65 | | 1.39 | 12.51 | 4.98 | |
| 73 | | 0.26 | 10.90 | 4.61 | |

V Xylitol Production by Fermentation of Silvergrass Xylose Hydrolysate without Detoxification Using *Candida* sp. Strain The fermentation medium is a silvergrass hydrolysate pretreated by dilute acid. For pretreatment, the concentration of the dilute acid is 1-4%, the operation temperature is 130° C., and the reaction time is 15 min at this temperature. In this case, NaOH is added to adjust the pH value of the hydrolysate to be 6.0, the fermentation temperature is controlled at 30° C., the agitation of the incubator is maintained at 100 rpm, and the ratio of the inocula size of the culture and the volume of the fermentation medium is 1:6 (v/v). The content of xylose in the silvergrass hydrolysate is 17.5-23.14 g/L, the content of the inhibitor furfural is 0.17-0.67 g/L, the amount of xylitol produced is 5.59-6.13 g/L, and the overall utilization of xylose is 97%, as shown in Table 3.

TABLE 3

Xylitol production by fermentation of silvergrass hydrolysate without detoxification

| time (h) | glucose (g/L) | xylose (g/L) | xylitol (g/L) | ethanol (g/L) | furfural (g/L) |
| --- | --- | --- | --- | --- | --- |
| 0 | 1.80 | 17.45 | | 1.79 | 0.17 |
| 22 | | 2.48 | 5.59 | 3.27 | |
| 26 | | 0.72 | 5.58 | 3.35 | |
| 30 | | 0.45 | 5.28 | 2.88 | |
| 0 | 3.43 | 23.14 | | 1.91 | 0.67 |
| 22 | | 17.20 | 1.10 | 3.88 | |
| 26 | | 15.78 | 1.73 | 4.34 | |
| 30 | | 12.50 | 2.61 | 4.70 | |
| 46 | | 2.75 | 6.02 | 5.18 | |
| 50 | | 1.24 | 6.13 | 5.23 | |
| 70 | | 0.65 | 6.10 | 3.10 | |
| 78 | | | 6.19 | 2.20 | |

VI Xylitol Production by Fermentation of Pineapple Peel Xylose Hydrolysate without Detoxification Using *Candida* sp. Strain The fermentation medium is a pineapple peel hydrolysate pretreated by dilute acid. For pretreatment, the concentration of the dilute acid is 2%, the operation temperature is 130° C., and the reaction time is 15 min at this temperature. In this case, NaOH is added to adjust the pH value of the hydrolysate to be 6.0, the fermentation temperature is controlled at 30° C., the agitation of the incubator is maintained at 100 rpm, and the ratio of the inocula size of the culture and the volume of the fermentation medium is 1:6 (v/v). The content of xylose in the pineapple peel hydrolysate is 19.8 g/L, and after 65 hr of fermentation, the amount of xylitol produced is 7.5 g/L, and the overall utilization of xylose is up to 97.4%, as shown in Table 4.

TABLE 4

Xylitol production by fermentation of pineapple peel hydrolysate without detoxification

| time (h) | glucose (g/L) | xylose (g/L) | xylitol (g/L) | ethanol (g/L) | furfural (g/L) |
| --- | --- | --- | --- | --- | --- |
| 0 | 3.19 | 19.84 | | 2.00 | |
| 17 | | 17.91 | 2.51 | 3.00 | |
| 25 | | 14.86 | 1.46 | 3.12 | |
| 41 | | 7.61 | 4.29 | 3.50 | |
| 49 | | 4.24 | 5.48 | 3.64 | |
| 65 | | 1.67 | 7.52 | 3.72 | |
| 73 | | 0.95 | 6.20 | 3.38 | |

VII Xylitol Production by Fermentation of Napiergrass Xylose Hydrolysate without Detoxification Using *Candida* sp. Strain The fermentation medium is napiergrass hydrolysate obtained by a pretreatment process of acid-catalyzed steam explosion. Pretreatment conditions: the concentration of the dilute acid is 2%, the operation temperature is 180° C., the reaction time at this high temperature is 5 min, after which the reactor is immediately depressurized. The reaction mix is then separated by a solid-liquid separation equipment to get the liquid fraction as hydrolysate. In this case, NaOH is added into the napiergrass hydrolysate to adjust to pH 6.0, the fermentation temperature is controlled at 30° C., the agitation of the incubator is maintained at 100 rpm, the ratio of the inocula size of the culture and the volume of the fermentation medium is 1:6 (v/v). The content of xylose in the napiergrass hydrolysate is 15.55 g/L, the content of the inhibitor furfural is 1.19 g/L, and after 40 hr of fermentation, the amount of xylitol produced is 5.11 g/L, and the overall utilization of xylose is up to 95.2%, as shown in Table 5.

TABLE 5

Xylitol production by fermentation of napiergrass hydrolysate without detoxification

| time (h) | glucose (g/L) | xylose (g/L) | xylitol (g/L) | ethanol (g/L) | furfural (g/L) |
|---|---|---|---|---|---|
| 0 | 6.99 | 15.55 | | 1.34 | 1.19 |
| 16 | 0.21 | 10.62 | 1.57 | 5.04 | |
| 24 | | 7.06 | 2.89 | 5.42 | |
| 40 | | 1.39 | 5.11 | 5.78 | |
| 48 | | 0.41 | 3.74 | 4.66 | |
| 64 | | | | | |

As the compositions of lignocellulosic materials as mentioned above are very different from each other, among the compositions of the pretreated hydrolysates, in addition to the furfural having inhibitive effect on the strain, a trace amount of inhibitors of different kinds that have not been detected may exist. It can be known from the above that, the *Candida* strain of the present invention is applicable in xylose fermentation of various lignocellulosic hydrolysates without detoxification, and can achieve a utilization rate of xylose of higher than 95% while maintaining a reasonable efficiency for xylitol production, which indicates that the *Candida* strain of the present invention surely has a certain degree of tolerance to the fermentation inhibitors generally existing in the lignocellulosic hydrolysates, and if applied in the xylose fermentation, it will facilitate the simplification of the conditioning steps of the xylose-rich hydrolysates, thereby reducing the facilities investments for of the hydrolysate conditioning.

Although the specific embodiments have been illustrated and described above, it will be apparent to those skilled in the art that various modifications and variations can be made in the present invention without departing from the scope or spirit of the invention. Furthermore, the present invention is not limited to the particular forms, and covers all modifications and variations of this invention provided they fall within the scope of the following claims and their equivalents.

In view of the above, in terms of its general combination and features, the present invention has no been found in similar products, and has not been disclosed before its filing date. It indeed meets the requirements of a patent and we thus propose this application according to the provisions of the patent law.

What is claimed is:

1. A method for producing xylitol by fermentation of non-detoxified lignocellulosic hydrolysates, comprising:
   conducting a pretreatment process to obtain the non-detoxified lignocellulosic hydrolysates by using a twin-screw extruder to mix acids and xylose;
   adding an alkali agent into the non-detoxified lignocellulosic hydrolysates to adjust pH value between 4.5 and 7.0; and
   converting the xylose contained in the non-detoxified lignocellulosic hydrolysates into xylitol through a fermentation by using a yeast strain belonging to the *Candida* as a xylose fermentation strain.

2. The method according to claim 1, wherein the fermentation is carried out in presence of a carbon source selected from the group consisting of glucose, xylose, and xylose hydrolysate of a lignocellulosic biomass material.

3. The method according to claim 1, wherein a lignocellulosic material for the non-detoxified lignocellulosic hydrolysates is selected from the group consisting of rice straw, sugarcane bagasse, silvergrass, napiergrass, pineapple peel, switchgrass, wood, bamboo, and other lignocellulosic biomass materials.

\* \* \* \* \*